United States Patent [19]

Gyory et al.

[11] Patent Number: 5,169,383
[45] Date of Patent: Dec. 8, 1992

[54] CONTROL MEMBRANE FOR ELECTROTRANSPORT DRUG DELIVERY

[75] Inventors: J. Richard Gyory; Ronald P. Haak, both of San Jose; Felix Theeuwes, Los Altos, all of Calif.

[73] Assignee: ALZA Corporation, Palo Alto, Calif.

[21] Appl. No.: 571,577

[22] PCT Filed: Oct. 2, 1989

[86] PCT No.: PCT/US89/04318
§ 371 Date: Sep. 7, 1990
§ 102(e) Date: Sep. 7, 1990

[87] PCT Pub. No.: WO90/03825
PCT Pub. Date: Apr. 19, 1990

[51] Int. Cl.⁵ .............................................. A61N 1/30
[52] U.S. Cl. ..................................... 604/20; 128/798; 128/802
[58] Field of Search ................. 128/798, 802, 803; 604/20

[56] References Cited

U.S. PATENT DOCUMENTS

| | | | |
|---|---|---|---|
| 3,797,494 | 3/1974 | Zaffaroni | 128/268 |
| 4,144,317 | 3/1979 | Higuchi et al. | 424/21 |
| 4,274,420 | 6/1981 | Hymes | 128/641 |
| 4,325,367 | 4/1982 | Tapper | 128/207.21 |
| 4,391,278 | 7/1983 | Cahalan et al. | 128/640 |
| 4,419,092 | 12/1983 | Jacobsen et al. | 604/20 |
| 4,457,748 | 7/1984 | Lattin et al. | 604/20 |
| 4,474,570 | 10/1984 | Ariura et al. | 604/20 |
| 4,557,723 | 12/1985 | Sibalis | 604/20 |
| 4,573,996 | 3/1986 | Kwiatek | 604/897 |
| 4,622,031 | 11/1986 | Sibalis | 604/20 |
| 4,640,689 | 2/1987 | Sibalis | 604/20 |
| 4,673,565 | 6/1987 | DiLuccio et al. | 424/443 |
| 4,689,039 | 8/1987 | Masaki | 604/20 |
| 4,702,732 | 10/1987 | Powers et al. | 604/20 |
| 4,708,716 | 11/1987 | Sibalis | 604/20 |
| 4,713,050 | 12/1987 | Sibalis | 604/20 |
| 4,722,726 | 2/1988 | Sanderson et al. | 604/20 |
| 4,731,049 | 3/1988 | Parsi | 604/20 |
| 4,731,926 | 3/1988 | Sibalis | 29/877 |
| 4,842,577 | 6/1989 | Konno et al. | 604/20 |
| 4,940,456 | 7/1990 | Sibalis et al. | 604/20 |
| 5,080,646 | 1/1992 | Theeuwes et al. | 604/20 |

FOREIGN PATENT DOCUMENTS

| | | |
|---|---|---|
| 208395 | 1/1987 | European Pat. Off. . |
| 249343 | 12/1987 | European Pat. Off. . |
| 278474 | 8/1988 | European Pat. Off. . |
| 174605 | 11/1986 | United Kingdom . |

OTHER PUBLICATIONS

P. Tyle & B. Kari, "Iontophoretic Devices", *Drug Delivery Devices*, Marcel Dekker, Inc., New York, pp. 421–454 (1988).

Primary Examiner—Stephen C. Pellegrino
Assistant Examiner—Michael Rafa
Attorney, Agent, or Firm—D. Byron Miller; Edward L. Mandell; Steven F. Stone

[57] ABSTRACT

A membrane capable of controlling the rate at which an agent is released from an iontophoretic delivery device is provided. The membrane inhibits agent release from the delivery device when no electrical current is flowing and yet provides minimal impedance to electrically-assisted agent delivery. The membrane is useful both as a control membrane in an iontophoretic agent delivery device and as a test membrane for testing the performance characteristics of an iontophoretic agent delivery device in vitro.

53 Claims, 2 Drawing Sheets

CONTROL MEMBRANE FOR ELECTROTRANSPORT DRUG DELIVERY

TECHNICAL FIELD

This invention relates to a device and method for delivering an agent transdermally or transmucosally by iontophoresis. More particularly, this invention relates to an electrically powered iontophoretic delivery device having a control membrane capable of inhibiting the release of agent from the device when the power is turned off while allowing agent delivery when the power is turned on. The membrane is also suitable for testing the performance characteristics of an electrotransport agent delivery device in vitro.

BACKGROUND ART

Iontophoresis, according to Dorland's Illustrated Medical Dictionary, is defined to be "the introduction, by means of electric current, of ions of soluble salts into the tissues of the body for therapeutic purpose." Iontophoretic devices have been known since the early 1900's. British patent specification No. 410,009 (1934) describes an iontophoretic device which overcame one of the disadvantages of such early devices known to the art at that time, namely the requirement of a special low tension (low voltage) source of current which meant that the patient needed to be immobilized near such source. The device of that British specification was made by forming, from the electrodes and the material containing the medicament or drug to be delivered transdermally, a galvanic cell which itself produced the current necessary for iontophoretically delivering the medicament. This ambulatory device thus permitted iontophoretic drug delivery with substantially less interference with the patient's daily activities.

More recently, a number of United States patents have issued in the iontophoresis field, indicating a renewed interest in this mode of drug delivery. For example, U.S. Pat. No. 3,991,755 issued to Vernon et al; U.S. Pat. No. 4,141,359 issued to Jacobsen et al; U.S. Pat. No. 4,398,545 issued to Wilson; and U.S. Pat. No. 4,250,878 issued to Jacobsen disclose examples of iontophoretic devices and some applications thereof. The iontophoresis process has been found to be useful in the transdermal administration of medicaments or drugs including lidocaine hydrochloride, hydrocortisone, fluoride, penicillin, dexamethasone sodium phosphate, insulin and many other drugs. Perhaps the most common use of iontophoresis is in diagnosing cystic fibrosis by delivering pilocarpine salts iontophoretically. The pilocarpine stimulates sweat production; the sweat is collected and analyzed for its chloride content to detect the presence of the disease.

In presently known iontophoretic devices, at least two electrodes are used. Both of these electrodes are disposed so as to be in intimate electrical contact with some portion of the skin of the body. One electrode, called the active or donor electrode, is the electrode from which the ionic substance, medicament, drug precursor or drug is delivered into the body by electrodiffusion. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be driven into the body is positively charged, then the positive electrode (the anode) will be the active electrode and the negative electrode (the cathode) will serve to complete the circuit. If the ionic substance to be delivered is negatively charged, then the negative electrode will be the active electrode and the positive electrode will be the counter electrode.

Alternatively, both the anode and cathode may be used to deliver drugs of opposite charge into the body. In such a case, both electrodes are considered to be active or donor electrodes. For example, the positive electrode (the anode) can drive a positively charged ionic substance into the body while the negative electrode (the cathode) can drive a negatively charged ionic substance into the body.

It is also known that iontophoretic delivery devices can be used to deliver an uncharged drug or agent into the body. This is accomplished by a process called electro-osmosis. Electro-osmosis is the volume flow of a liquid (e.g., a liquid containing the uncharged drug or agent) through the skin induced by the presence of an electric field imposed across the skin.

Furthermore, existing iontophoresis devices generally require a reservoir or source of the beneficial agent (which is preferably an ionized or ionizable agent or a precursor of such agent) to be iontophoretically delivered into the body. Examples of such reservoirs or sources of ionized or ionizable agents include a pouch as described in the previously mentioned Jacobsen U.S. Pat. No. 4,250,878, or a pre-formed gel body as described in Webster U.S. Pat. No. 4,382,529. Such drug reservoirs are electrically connected to the anode or the cathode of an iontophoresis device to provide a fixed or renewable source of one or more desired agents.

There is a continuing need to develop an iontophoretic drug delivery device with improved characteristics and specifically with improved control over the drug delivery profile. Conventional microporous ultrafiltration-type membranes have been used to control the rate at which agent (i.e., drug) is released from a passive transdermal or transmucosal delivery device. Passive delivery devices deliver drug or other beneficial agent through the skin by diffusion. These passive delivery devices are driven by a drug concentration gradient (i.e., the concentration of drug in the drug reservoir of the device is greater than the concentration of drug in the skin of the patient). While conventional semipermeable ultrafiltration-type membranes have been suggested for use in iontophoretic delivery devices (e.g., in Parsi U.S. Pat. No. 4,731,049 and Sibalis U.S. Pat. No. 4,460,689) they have been found to be unsuitable for use in portable battery-powered iontophoretic delivery devices because of their high electrical resistivity (i.e., resistivity to ionic transport). Therefore, there is a need for a membrane having low electrical resistivity which may be used to control the rate at which agent is released from an electrically-powered iontophoretic agent delivery device.

There is also a need for a control membrane in an iontophoretic drug delivery device which can substantially prevent passive release of drug from the device when the device is placed on the patient's body. Such a membrane also would have important advantages when delivering highly potent drugs which might otherwise become harmful to the patient if present at greater than predetermined plasma concentrations. The membrane would prevent too much drug from being delivered, if for example, the delivery device is inadvertently placed on cut or abraded skin or on a body surface which has somehow been compromised. Further, such a membrane would permit safer handling of the device during manufacture and use.

Such a membrane, by eliminating or at least greatly reducing passive transport, would also allow the drug delivery rate to be substantially reduced when the power to the iontophoretic delivery device is turned off. Thus, the membrane would have particular utility in both iontophoretic delivery devices which are turned on and off by the patient for "on-demand" delivery of a beneficial agent (e.g., an anesthetic or other pain killing agent) or in iontophoretic delivery devices having a control circuit which alternates drug delivery pulses with periods during which no drug is delivered. Since the membrane would substantially reduce the rate at which beneficial agent is passively delivered from the device, the membrane would allow a more precise patterned drug delivery profile.

Along with the growing interest in the development of iontophoretic delivery devices, there has been a growing need for improved techniques of testing the performance characteristics of the devices. For example, state of the art techniques for measuring the in vitro agent release rates of passive transdermal systems are inadequate for testing the agent release rates of electrically powered iontophoretic delivery devices. Typically, such testing involves placing the passive delivery system on either a section of human cadaver skin or on a synthetic membrane which exhibits passive drug diffusion characteristics similar to that of skin. Examples of such membranes include a copolyester membrane sold by E.I. DuPont de Nemours of Wilmington, Del. under the tradename Hytrel ® or an ethylene vinyl acetate copolymer such as EVA 9. The other side of the skin or membrane is in contact with an aqueous receiving medium. The drug is delivered from the passive delivery system through the skin or membrane into the aqueous medium where it can be collected for measurement. Unfortunately, these passive delivery test membranes do not closely approach the electrically-assisted ion transport characteristics of skin and therefore cannot be used to accurately predict the in vivo performance characteristics of an iontophoretic delivery device. In addition, cadaver skin exhibits an unacceptably high level of variation (when measuring device stability) and sufficient quantities of cadaver skin are not always readily available. Thus, there is a need for a synthetic membrane which exhibits electrically-assisted ionic transport properties similar to those of skin and which therefore can be used to test the performance characteristics of an iontophoretic agent delivery device in vitro.

DISCLOSURE OF THE INVENTION

It is an object of this invention to provide an improved control membrane and method for controlling the rate at which agent is released from an electrically powered iontophoretic delivery device.

It is another object of this invention to provide a safety mechanism for an electrically powered iontophoretic delivery device to ensure that agent is only released during those periods when the power is turned on.

It is a further object of this invention to provide a membrane which will allow passage of agent at a predetermined rate when the power is turned on and which acts as a barrier to the passage of agent when the power is turned off.

Another object of this invention is to provide a membrane which closely approximates the electrically-assisted ion transport properties of skin and which can therefore be used as a skin model for measuring the performance characteristics of an electrically powered iontophoretic agent delivery device in vitro.

These and other objects are met by a membrane for controlling agent delivery from an iontophoretic agent delivery device. The device has an agent-containing reservoir which is connectable to a source of electrical power for driving the agent from the reservoir and through a body surface, such as skin or a mucosal membrane. The membrane is interposed between the agent reservoir and the body surface. The membrane permits electrically-assisted flux ($J_{EK}$) of the agent therethrough while substantially preventing passive flux ($J_p$) of agent therethrough. In addition, the membrane exhibits a $(J_{EK}+J_p)/J_p$ ratio of at least about 4, a voltage drop across the membrane of less than about 1 volt and a $J_p$ of less than about 100 $\mu$g/hr-cm$^2$. Preferably, the membrane exhibits a $(J_{EK}+J_p)/J_p$ ratio of at least about 6, a voltage drop across the membrane of less than about 0.1 volts and a $J_p$ of less than about 50 $\mu$g/hr-cm$^2$.

Also provided is a membrane for testing the performance characteristics of an iontophoretic agent delivery device. The device has an agent-containing reservoir which is connectable to a source of electrical power for driving the agent from the reservoir and through a body surface, such as skin or a mucosal membrane. The membrane permits electrically-assisted flux $J_{EK}$) of agent therethrough while substantially preventing passive flux ($J_p$) of agent therethrough. The membrane exhibits a $J_{EK}+J_p)/J_p$ ratio of at least about 4, a voltage drop across the membrane of less than about 10 volts and a $J_p$ of less than about 100 $\mu$g/hr-cm$^2$.

Preferably, the membrane exhibits a $(J_{EK}+J_p)/J_p$ ratio of at least about 6, a voltage drop across the membrane of less than about 1 volt and a $J_p$ of less than about 50 $\mu$g/hr-cm$^2$.

MODES FOR CARRYING OUT THE INVENTION

Figure 1:
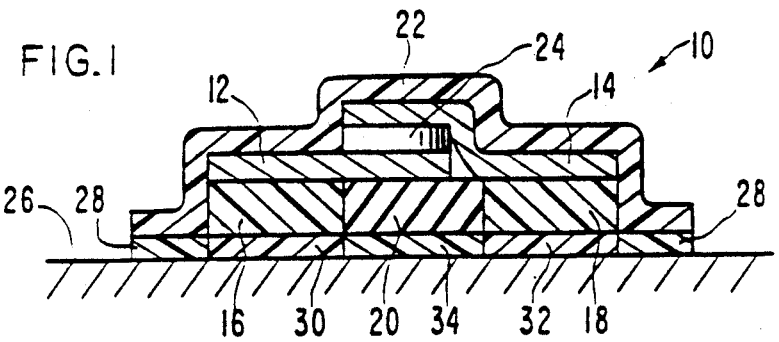
FIG. 1 is a cross sectional view of one embodiment of a device for iontophoretic delivery of a beneficial agent, the device having a control membrane according to the present invention.

The membrane of the present invention inhibits the release of drug due to passive diffusion when the device is positioned on the patient's body. The flux due to passive diffusion is termed $J_p$. While the delivery of drug due to passive diffusion from an electrically powered iontophoretic delivery device is not usually a problem since the drugs delivered by such devices do not easily penetrate the skin via passive diffusion, if the skin is compromised in some manner, such as by being cut or scraped, a harmfully large dose of drug could be delivered. In general, the control membrane of the present invention limits the steady state passive diffusion rate ($J_p$) of agent therethrough to a level below about 100 μg/hr-cm² when the device is positioned on the patient's body. Preferably the steady state passive diffusion rate ($J$)r is below about 50 μg/hr-cm² and most preferably below about 10 μg/hr-cm².

The above limits for the steady state passive diffusion rate should not be exceeded regardless of the concentration gradient of drug or agent across the membrane. In most cases, the concentration of drug in the drug reservoir of the iontophoretic delivery device will be at or near saturation while the concentration of drug in the body surface of the patient will be extremely low. Thus, even at such a maximum concentration gradient, the steady state passive flux of drug should not exceed the above mentioned limits.

In order to determine whether a particular membrane meets the steady state passive diffusion characteristics mentioned above, the following measurement procedure may be used. The membrane is secured between the compartments of a two-compartment cell. One surface of the membrane is exposed to the donor compartment which contains an aqueous solution of the drug to be delivered. The concentration of drug in the donor compartment is 0.1 g/ml. The opposite surface of the membrane is in contact with the receptor compartment which contains a receptor solution composed of Dulbecco's phosphate buffered saline (pH 7) sold by Gibco Laboratories of Grand Island, N.Y., Catalogue No. 310-4040, and having a nominal NaCl concentration of 0.137 M. The solution in the donor compartment is in contact with an electrode, which is preferably composed of Ag/AgCl. Similarly, the receptor solution is in contact with an electrode, also preferably composed of Ag/AgCl. The electrodes are connected to opposite poles of a galvanostat capable of providing a constant level of electric current to the two electrodes. $J_p$ is measured using this apparatus with the galvanostat providing no electric current to the electrodes.

When measuring passive flux, there is always an initial transient period before the passive flux reaches steady state. The term $J_p$ used herein refers to the steady state passive flux of drug through the membrane and therefore the flux should be measured at least about an hour after the membrane is exposed to the drug concentration gradient between the donor and receptor solutions in order to be certain the flux has reached a steady state level.

When a control membrane according to this invention is incorporated into an iontophoretic delivery device, the passive release of drug from the device is substantially prevented and therefore the release of drug is predominantly controlled by the magnitude of the electrical current. Therefore, even if the skin is compromised, the amount of drug delivered by the iontophoretic device is controlled to a safe level.

In addition to limiting the passive diffusion of drug, the control membrane of this invention exhibits a substantially higher electrically-assisted flux of drug than the flux of drug due to passive diffusion. The steady state electrically-assisted flux or electrokinetic flux $J_{EK}$, is the sum of the fluxes due to electromigration and electro-osmosis. As mentioned above, the flux due to passive diffusion is termed $J_p$. Thus, the total flux ($J_T$) occurring during electrotransport is equal to the sum of the electrically-assisted flux ($J_{EK}$) and the flux due to passive diffusion ($J_p$). Thus, J equals the sum of $J_{EK}$ and $J_p$. Hereinafter, the term $J_T$ is used interchangeably with the expression ($J_{EK}+J_p$). Likewise, the ratio $J_T/J_p$ is equal to, and is hereinafter used interchangeably with, the ratio ($J_{EK}+J_p$)/$J_p$.

The control membrane of the present invention has a $J_T/J_p$ ratio of at least about 4, preferably at least about 6, and most preferably at least about 10. Like the steady state passive flux ($J_p$), the steady state total flux ($J_T$) likewise will be effected by the drug concentration gradient across the membrane. This is so because the total flux ($J_T$) includes the passive flux ($J_p$), which passive flux is effected by the drug concentration gradient across the membrane. The above-mentioned limits for the $J_T/J_p$ ratio should be met or exceeded regardless of the drug concentration gradient across the membrane.

In order to determine whether a particular membrane meets the above-mentioned requirements for the $J_T/J_p$ ratio, the steady state total flux ($J_T$) may be measured using the same apparatus used to measure $J_p$ and described above. However, when measuring $J_T$, the electrodes of the two compartment cell are connected to a galvanostat which supplies a constant electric current of 100 μA/cm² of membrane. A suitable galvanostat is manufactured by EG&G Princeton Applied Research, Model No. 363. As with the passive flux, the total flux ($J_T$) used herein refers to the steady state total flux and therefore should be measured at least about an hour after the membrane is exposed to the drug concentration gradient between the donor and receptor solutions.

In addition to the $J_p$ value and the $J_T/J_p$ ratio, the control membrane of the present invention should have a sufficiently low voltage drop across the membrane to enable a portable power source, such as a low voltage (i.e., up to about 20 volts) battery, to deliver beneficial agent to the skin or mucosa of a patient. A control membrane for use in an iontophoretic delivery device should exhibit a voltage drop of less than about 1 volt, and preferably less than about 0.1 volts. For membranes which are used to test the performance characteristics (e.g., agent delivery rate) of an iontophoretic delivery device in vitro a low voltage drop is not as critical since for in vitro testing of iontophoretic delivery devices a higher voltage power source can be used without additional inconvenience For such testing, the membrane should exhibit a voltage drop of less than about 10 volts, preferably less than about 1 volt, and most preferably less than about 0.1 volts. The voltage drop across a membrane is measured by placing the reference electrodes (e.g., Ag/AgCl electrodes) of a potentiometer (e.g., Dynascan Corp., Model No. 2905) on either side of the membrane while 100 μA of current per square centimeter of membrane is being passed and recording the potential difference.

One embodiment of a control membrane according to the present invention is a specially modified cellulose acetate membrane. Most conventional microporous cellulose acetate membranes are unsuitable for use as a control membrane according to the present because they exhibit an unacceptably high voltage drop across the membrane (e.g., greater than 30 volts). However, conventional cellulose acetate resins can be processed in accordance with the following procedure to achieve an acceptable control membrane. The control membrane is made by dissolving in a solvent composed of methylene chloride and methanol (1) about 60 to 95 parts by weight of cellulose acetate resin (e.g., cellulose acetate 398-10 having an acetyl content of 39.8 wt % and a falling ball viscosity of 10 seconds, manufactured by Eastman Kodak Co. of Rochester, N.Y.) and (2) about 5 to 40 parts by weight of a water soluble material having a molecular weight at least as great as the molecular weight of the drug or beneficial agent being iontophoretically delivered. Suitable water soluble materials include polyethylene glycol, non-cross linked polyvinylpyrrolidone, polyvinylalcohol and water soluble starch derivatives such as hydroxypropylmethyl cellulose and hydroxyethyl cellulose. The mixture is solvent cast to form a membrane and the solvent is allowed to evaporate. The membrane is then soaked overnight in water in order to leach out substantially all of the water soluble material. This leaves a membrane composed substantially entirely of e.g., cellulose acetate and having a pore volume of about 5 to 40%.

A second embodiment of a control membrane according to the present invention is a composite membrane comprising a mixture of a hydrophobic microporous polymer and a selected amount of a hydrophilic polymer. In general, the composite membrane of this embodiment contains about 10 to about 30 vol % hydrophilic polymer, preferably about 15 to about 25 vol % hydrophilic polymer, and most preferably about 20 vol % hydrophilic polymer. The above ranges for volume percent hydrophilic polymer should be used only as a rough guide since hydrophilic resin loadings outside these ranges may still provide satisfactory results when using certain hydrophilic resins. In addition to the hydrophilic polymer, the composite membrane may optionally contain standard fillers, surfactants to aid in improving the wetting characteristics of the membrane, leachable pore-forming agents, fibers or other fillers used as reinforcing agents, as well as a loading of the drug or other beneficial agent being delivered by the iontophoretic delivery device. The composite membrane can be manufactured by blending the hydrophobic polymer, the hydrophilic polymer and any fillers using standard techniques and then forming a membrane by solvent casting, melt processing or extrusion of the polymer blend.

The process of blending a hydrophilic resin into a hydrophobic matrix actually enhances the $J_T/J_p$ ratio of the membrane. Thicker membranes also exhibit a larger $J_T/J_p$ ratio since the passive flux decreases for thicker membranes without affecting the electrokinetic flux. However, a higher voltage is required to maintain the electrokinetic flux.

As used herein, the term "hydrophobic polymer" refers to polymers having an equilibrium water content of less than about 10%. Suitable hydrophobic polymeric materials for use in the control membrane of the present invention include without limitation, polycarbonates, i.e., linear polyesters of carbonic acids in which carbonate groups recur in the polymer chain by phosgenation of a dihydroxy aromatic such as bisphenol A, polyvinylchlorides, polyamides such as polyhexamethylene adipamide and other such polyamides commonly known as "nylon", modacrylic copolymers such as those formed of polyvinylchloride and acrylonitrile, and styrene-acrylic acid copolymers, polysulfones such as those characterized by diphenylene sulfone groups in the linear chain thereof, halogenated polymers such as polyvinylidene fluoride and polyvinylfluoride, polychloroethers and thermoplastic polyethers, acetal polymers such as polyformaldehyde, acrylic resins such as polyacrylonitrile, polymethyl methacrylate and poly n-butyl methacrylate, polyurethanes, polyimides, polybenzimidazoles, polyvinyl acetate, aromatic and aliphatic polyethers, cellulose esters such as cellulose triacetate, epoxy resins, olefins such as polyethylene and polypropylene, porous rubber, poly(ethylene oxides) which are sufficiently cross-linked to have an equilibrium water content of less than about 10%, polyvinylpyrrolidones which are sufficiently cross-linked to have an equilibrium water content of less than about 10%, poly(vinyl alcohols) which are sufficiently cross-linked to have an equilibrium water content of less than about 10%; derivatives of polystyrene such as poly(sodium styrenesulfonate) and polyvinylbenzyltrimethyl- ammonium chloride, poly(hydroxyethyl methacrylate), poly(isobutyl vinyl ether), polyisoprenes, polyalkenes, ethylene vinyl acetate copolymers, particularly those having 1-40 weight percent vinyl acetate content, such as those described in U.S. Pat. No. 4,144,317, incorporated herein by reference, polyamides, and polyurethanes. This list is merely exemplary of the materials suited for use in this invention. A more extensive list can be found in J. R. Scott & W. J. Roff, Handbook of Common Polymers (CRC Press, 1971) and in patents disclosing suitable materials for use in manufacturing microporous membranes such as U.S. Pat. No. 3,797,494, incorporated herein by reference.

As used herein, the term "hydrophilic resin" refers to resins which are at least water wetable but not necessarily water soluble and having an equilibrium water content of greater than about 10% and preferably greater than about 20%. Suitable hydrophilic resins for use in the control membrane of the present invention include materials such as polyvinylpyrrolidone, polyethylene oxides, polyox, polyox blended with polyacrylic acid or Carbopol ®, cellulose derivatives such as hydroxypropyl methyl cellulose, hydroxyethyl cellulose, hydroxypropyl cellulose, pectin, starch, guar gum, locust bean gum, and the like, along with blends thereof. Particularly suitable hydrophilic materials are ion exchange resins having a degree of cross-linking providing an equilibrium water content greater than about 10%. Ion exchange resins and their properties are described in The Kirk-Othmer Encyclopedia of Chemical Technology, 3rd Edition, Volume 13, pps. 678 to 705, John Wiley & Sons (1981).

Particularly preferred ion exchange resins have ion exchange functional groups such as sulfonic acid, carboxylic acid, imidodiacetic acid and quaternary amines. These include, without limitation, the commercially available cation and anion exchange resins listed in the tables below.

| NAME (BACKBONE) | FORM | Cation Exchange Resins | | | | |
|---|---|---|---|---|---|---|
| | | SIZE mesh | DRY meq/g | RESIN BED mea/mL | MOISTURE % of total | PORE SIZE |
| AG 50W-X12* (Sulfonic acid) | H | 100-200 | 5 | 2.3 | 42-48 | small |

-continued

| | | Cation Exchange Resins | | | | |
|---|---|---|---|---|---|---|
| NAME (BACKBONE) | FORM | SIZE mesh | DRY meq/g | RESIN BED mea/mL | MOISTURE % of total | PORE SIZE |
| Bio-Rex ®70* (Carboxylic acid) | Na | 200–400 | 10.2 | 3.3 | 65–74 | large |
| Chelex ®100* Chelating resin (Iminodiacetic acid) | Na | 100–200 | 2.9 | 0.7 | 71–76 | large |
| Amberlite IR-120** (Sulfonic acid) | H | 20–50 | 5.0 | 1.8 | 49–55 | medium |

| | | Anion Exchange Resins | | | | |
|---|---|---|---|---|---|---|
| NAME (BACKBONE) | FORM | SIZE mesh | DRY meq/g | RESIN BED mea/mL | MOISTURE % of total | PORE SIZE |
| AG 1-X8* ($R_4N^+$) | Cl | 20–50 | 3.2 | 1.4 | 39–45 | medium |
| Amberlite IRA-400** ($RN(CH_3)_3^+$) | Cl | 20–50 | 3.3 | 1.2 | 42–48 | medium |

*sold by Bio-Rad of Richmond, CA
**sold by Mallinckrodt of St. Louis, MI

This invention has utility in connection with the delivery of drugs within the broad class normally delivered through body surfaces and membranes, including skin, mucosa and nails. As used herein, the expressions "agent" and "drug" are used interchangeably and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, anti depressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, polypeptides and other macromolecules, psychostimulants, sedatives and tranquilizers.

The device of the present invention can be used to deliver, in a controlled manner, the following drugs: baclofen, betamethasone, beclomethasone, dobutamine, doxazosin, droperidol, fentanyl, sufentanil, lidocaine, methotrexate, miconazole, nicardapine, prazosin, piroxicam, verapamil, tetracaine, diltiazem, indomethacin, ketoprofen, hydrocortisone, metaclopramide, terbutaline and encainide.

More preferably, the invention is useful in the controlled delivery of peptides, polypeptides and other macromolecules typically having a molecular weight of at least about 500 daltons, and typically a molecular weight in the range of about 500 to 40,000 daltons. Specific examples of peptides and proteins in this size range include, without limitation, LHRH, LHRH analogs such as buserelin, gonadorelin, naphrelin and leuprolide, GHRH, insulin, heparin, calcitonin, endorphin, TRH, NT-36 (chemical name: N=[[(s)-4-oxo-2-azetidinyl]carbonyl]-L-histidyl-L-prolinamide), liprecin, pituitary hormones (e.g., HGH, HMG, HCG, desmopressin acetate, etc.,), follicle luteoids, oANF, growth factor releasing factor (GFRF), βMSH, somatostatin, bradykinin, somatotropin, platelet-derived growth factor, asparaginase, bleomycin sulfate, chymopapain, cholecystokinin, chorionic gonadotropin, corticotropin (ACTH) erythropoietin, epoprostenol (platelet aggregation inhibitor), glucagon, hyaluronidase, interferon, interleukin-2, menotropins (urofollitropin (FSH) and LH), oxytocin, streptokinase, tissue plasminogen activator, urokinase, vasopressin, ACTH analogs, ANP, ANP vasopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 anti-trypsin (recombinant).

It is most preferable to use a water soluble salt of the drug or agent to be delivered.

The invention is best understood with reference to the accompanying drawings. In general terms, this invention can be used in conjunction with any known iontophoretic agent delivery device including those described in U.S. Pat. Nos. 4,325,367; 4,474,570; 4,557,723; 4,640,689; and 4,708,716; all of which are incorporated herein by reference. Similarly, this invention can be utilized with any known iontophoretic electrode which is adapted to be attached to an external power source, including those described in U.S. Pat. Nos. 4,274,420; 4,391,278; 4,419,092; and 4,702,732; all of which are incorporated herein by reference. The control membrane of this invention can be manufactured as an integral part of an iontophoretic delivery device or electrode, or it can be manufactured separately with adhesive layers or some suitable means for adhering so that it may subsequently be affixed to an iontophoretic delivery device or electrode.

FIG. 1 illustrates an embodiment of an electrotransport device 10 utilizing the composite membrane of this invention. Device 10 has two current conducting members, referred to herein as a donor electrode 12 and a counter electrode 14. The electrodes can be metal foils, a polymeric matrix loaded with metal powder, powdered graphite or carbon fibers, or any other electrically conductive material. The donor electrode 12 and the counter electrode 14 are positioned adjacent to the donor electrode pad 16 and the counter electrode pad 18, respectively. In this embodiment, the donor electrode pad 16 contains the agent to be delivered. The pads 16 and 18 can be polymeric matrices or gel matrices, for example, and are separated by an insulator 20 made of a non-conducting polymeric material. Device 10 has a backing layer 22 made of an electrically insulating or non-conductive material such as is commonly used in passive transdermal systems. Electrical power is supplied by power source 24, which can be a battery or a series of batteries, such that the electrode 12 is in electrical contact with one pole of the power source 24 and electrode 14 is in electrical contact with the opposite pole. The device 10 is adhered to the body surface 26 by means of a peripheral adhesive layer 28. The device 10 normally includes a strippable release liner, not shown, which is removed just prior to application to the body surface.

The control membrane of the present invention is designated by the numeral 30 and is positioned between the doner electrode pad 16 and the body surface 26, so as to control the rate at which drug is released from the pad 16. In a typical device 10, the donor electrode pad 16 contains an ionizable supply of the drug to be delivered and the counter electrode pad 18 contains a suitable electrolyte. Alternatively, device 10 contains an ionizable supply of drug in both electrode pads 16 and 18 and in that manner both pads 16 and 18 would function as donor electrode pads. For example, positive ions could be introduced into tissues from the anode (positive electrode), while negative ions could be introduced from the cathode (negative pole). In that instance, a second control membrane 32 according to the present invention is positioned between the electrode pad 18 and the body surface 26.

Layer 34 is composed of a non-conducting material which acts as a barrier to prevent short-circuiting of the device 10. Layer 34 can be an air gap, a non-ion conducting adhesive or other suitable barrier to ion flow. Alternatively, membranes 30 and 32 and layer 34 may be comprised of a single continuous membrane having different ion transport properties (i.e., a single membrane having portions 30 and 32 with a low resistance to ionic transport and a portion 34 having a high resistance to ionic transport).

Figure 2:
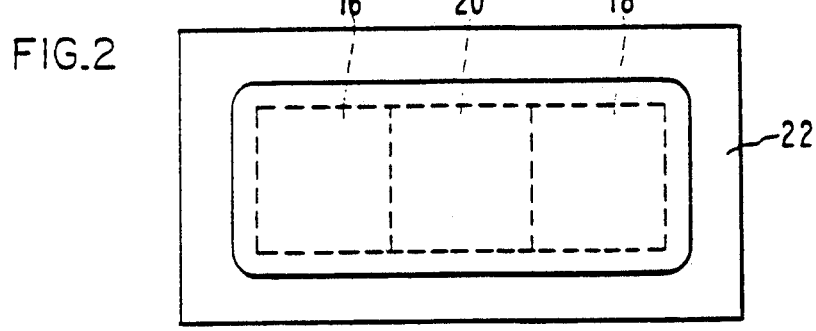
FIG. 2 is a top view of the embodiment shown in FIG. 1, with parts shown in phantom.

FIG. 2 illustrates a top view of the device 10 and shows the parallel alignment of the pads 16 and 18 and the insulator 20. In this configuration, the control membranes 30 and 32 are rectangular in shape. However, the present invention is not limited to any particular electrode shape or configuration. For example, the control membrane of the present invention could be used in an iontophoretic delivery device having electrodes which are aligned peripherally (i.e., the donor electrode is centrally positioned while the counter electrode surrounds, in spaced-apart relation, the donor electrode), in a circular configuration for example, and the composite membrane would be shaped accordingly.

The size of the control membranes 30 and 32 of this invention can vary with the size of the electrode pads 16 and 18. Generally, the electrode pads will have a combined area within the range of from less than 1 cm$^2$ to greater than 200 cm$^2$, and preferably about 5-50 cm$^2$. Similarly, the composite membrane will typically be within that range.

In general, the control membrane of the present invention will have a thickness in the range of about 1 to 15 mills, preferably within the range of about 3 to 5 mils.

Figure 3:
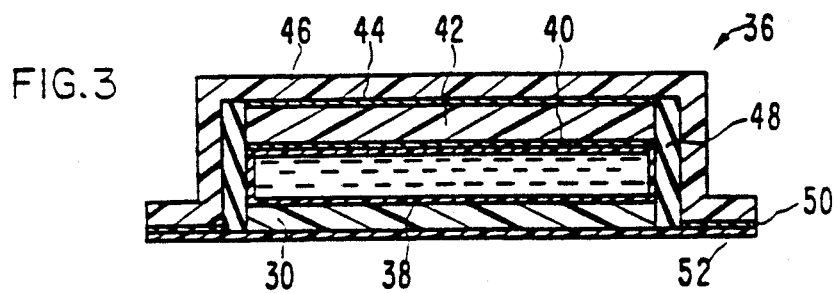
FIG. 3 is a cross sectional view of another embodiment of an iontophoretic delivery device according to the present invention.

FIG. 3 illustrates another embodiment of an electrically powered iontophoretic delivery device, designated by the numeral 36, and suitable for use with the control membrane 30 of this invention. Device 36 has an agent reservoir 38 which can be in the form of a flexible bag as shown or a polymer matrix as in device 10. A first current conducting member 40 is positioned between reservoir 38 and battery 42. A second current conducting member 44 is positioned between battery 42 and a conductive backing member 46. The device 36 has an electrically insulating member 48 and a peripheral ion-conducting adhesive layer 50. The device 36 is packaged with a strippable release liner 52. Suitable materials for use in the layers of device 36, except for the control membrane 30, are disclosed in U.S. Pat. No. 4,713,050, incorporated herein by reference.

Figure 4:
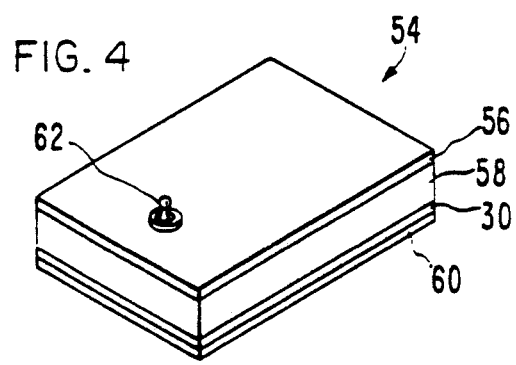
FIG. 4 is a perspective view of a single electrode of an iontophoretic agent delivery device, the electrode having a control membrane in accordance with the present invention.

FIG. 4 illustrates an iontophoresis electrode 54 (i.e., a donor electrode) suitable for use with the control membrane 30 of this invention. Electrode 54 has a current conducting member 56, an agent reservoir 58 and a control membrane 30 according to the present invention. The electrode 54 adheres to the body surface by means of an ion-conducting adhesive layer 60. The electrode 54 has a fastener 62 by which it can be connected to an external power source. Suitable materials for use in the electrode 54, except for the control membrane 30, are disclosed in U.S. Pat. No. 4,274,420, incorporated herein by reference.

The control membrane of the present invention can also be used for testing the performance characteristics (e.g., drug delivery rate from the iontophoretic delivery device, the amount of agent contained in the device, the magnitude of electrical current flowing through the device, the agent discharge profile as a function of time, and the discharge capacity of the electrical power source, etc.) of an electrically powered iontophoretic delivery device in vitro This is especially useful for predicting the actual in vivo performance characteristics of the iontophoretic delivery device For this use, it is desirable that the membrane have both passive and electrically-assisted transport characteristics similar to that of skin. The control membrane of this invention meets these requirements.

An evaluation of the agent release characteristics of an iontophoretic delivery device using a control membrane according to this invention involves the placement of the device on the surface of the control membrane A reservoir of receptor solution is in contact with the opposite surface of the membrane. When the iontophoretic delivery device is placed on the membrane, passive transport (i.e., transport due to passive diffusion through the membrane when the power is turned off) of agent into the receptor solution is inhibited. When the power is turned on, the delivery device transports agent through the control membrane into the receptor solution where it is collected and measured.

Having thus generally described our invention, the following examples will further illustrate selected preferred embodiments.

EXAMPLE I

Composite membranes according to this invention were made using the following materials. Two hydrophobic polymers were used: ethylene vinyl acetate having 28 weight percent vinyl acetate content (EVA 28) and ethylene vinyl acetate having 40 weight percent vinyl acetate content (EVA 40). Three hydrophilic resins were used: (1) polyvinylpyrrolidone (PVP) having an equilibrium water content of about 100%, a wettable resin which picks up a slight positive charge due to hydrogen ion adsorption at amine sites; (2) Bio-Rex ®70, a macroreticular acrylic polymer based carboxylic acid cation exchange resin made by Bio-Rad Laboratories, of Richmond, Calif.; and (3) Chelex ®100, a styrene divinylbenzene lattice with paired imidodiacetate cation exchange groups also made by Bio-Rad Laboratories. Two particle sizes of Chelex ®100 were used: particles having a size smaller than 400 mesh and particles having a size in the range of 100–200 mesh. All films containing PVP were made with EVA 28 as the hydrophobic matrix material Membranes containing Bio-Rex ®70 and Chelex ®100 were made with EVA 40 as the hydrophobic matrix material. Membranes were made by solvent casting or melt processing. All membranes containing PVP were made by standard melt processing techniques and all membranes containing Bio-Rex ®70 were solvent cast from methylene chloride and dried at ambient conditions. Both methods of preparation were used for membranes containing Chelex ®100.

The transport properties of these membranes were evaluated by measuring the passive and electrically-assisted flux of metoclopramide (MCP) across each membrane. This was done using a two compartment cell. The membranes were each secured between the donor and receptor compartments of the cell. The donor compartment contained an electrode composed of Ag/AgCl while the receptor compartment contained an electrode also composed of Ag/AgCl. An MCP solution having a concentration of 0.1 g MCP/ml was placed in the donor compartment and the receptor compartment was filled with Dulbecco's phosphate buffered saline (pH 7). Dulbecco's phosphate buffered saline (DPBS) has a nominal NaCl concentration of 0.137 M and is sold by Gibco Laboratories of Grand Island, N.Y., Catalogue No. 310-4040. The experimental temperature for all experiments was 32° C. Cells operating under passive conditions had zero current applied while cells operating under active or electrically-assisted conditions had 100 $\mu A/cm^2$ of current applied such that positive ions migrated from the donor to the receptor compartment and negative ions migrated from the receptor to the donor compartment. In this manner, the electrode next to the donor solution was the anode and the electrode next to the receptor solution was the cathode. The receptor solution was periodically sampled after reaching steady state flux and evaluated for MCP content. At sampling time, all of the receptor solution was removed and replaced with fresh DPBS. The samples were analyzed for MCP content using UV-absorbance at 310 nm.

Figure 5:
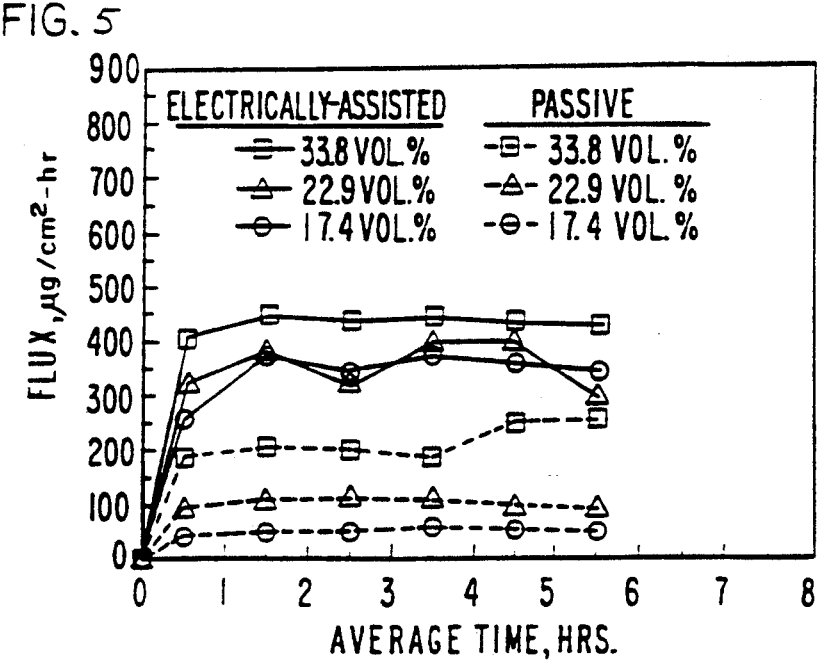
FIG. 5 is a graph comparing the electrically-assisted and passive fluxes of metoclopramide through various membranes of the present invention.

Electrically-assisted and passive flux profiles of MCP for three volume loadings of Bio-Rex ®70 in EVA 40 are shown in FIG. 5. As the Bio-Rex ®70 resin loading was increased beyond about 23 vol %, the $J_T/J_p$ ratio fell below about 3.5. A Bio-Rex ®70 resin loading of 33.8 vol % was tested and yielded a $J_T/J_p$ ratio of only 2, well outside the scope of the present invention. Accordingly, when using Bio-Rex ®70 and EVA 40 composite membranes, the Bio-Rex ®70 resin loading should be kept below about 23 vol %.

Similarly, when using EVA 28 and PVP composite membranes, the PVP resin loading should be kept below about 12 to 15 vol %.

Table I presents the steady state $J_T/J_p$ ratios for the membranes tested.

TABLE I

| Polymer | Resin | Resin Loading, vol % | $J_T/J_p$ Ratio |
|---|---|---|---|
| EVA 40 | Bio-Rex ®70 | 17.4 | 7 |
| | | 22.9 | 3.5 |
| | | 33.8 | 2 |
| EVA 28 | PVP | 12 | 7.4 |
| | | 18 | 1.9 |
| | | 25 | 1.4 |
| | | 34 | 1.3 |
| EVA 40 | Chelex ®100 (100–200 mesh) | 18.5 | 46 ± 17 |
| | | 24.2 | 21 ± 3 |
| | | 46.4 | 19 ± 3 |

Membranes incorporating Chelex ®100 (particle size of 100–200 mesh) and Chelex ®100 (particle size smaller than 400 mesh) exhibit an electrically-assisted steady state flux of about 300 $\mu g/cm^2 hr$. However, the membranes prepared using the larger (100–200 mesh) particle size resin exhibit appreciably higher passive flux of MCP.

COMPARATIVE EXAMPLE A

Commercial microporous ultrafiltration-type membranes, of the kind disclosed in Parsi U.S Pat. No. 4,731,049 and Sibalis U.S. Pat. No. 4,460,689, were tested to determine their suitability for use as a control membrane in an iontophoretic drug delivery device. The membranes tested included (Celgard ®) polypropylene and polyethylene based microporous membranes manufactured by Hoechst Celanese, of Charlotte, N.C.; Nuclepore polycarbonate and polyester microporous membranes, manufactured by Nuclepore Corp. of Pleasanton, Calif.; cellulose acetate membranes mixed with varying amounts of triacetin which was leached out by soaking the membranes overnight in water; and Vycor ® porous glass model No. 7930 manufactured by Corning Glass Works of Corning, N.Y., which was cut to various thicknesses. Pore sizes ranged from 40 Å for the porous Vycor ® to 0.2 $\mu m$ for Celgard ® and were undetermined for the cellulose acetate membranes. The transport properties of the membranes were evaluated as in Example I and are presented in Table II.

TABLE II

| Membrane | $J_p$ $\mu g/hr-cm^2$ | $J_T/J_p$ | Voltage Drop volts |
|---|---|---|---|
| Celgard 2400* | N/A | N/A | >30 |
| Celgard 2500* | N/A | N/A | >30 |
| Celgard K 380 | >1000 | 1.0 | 0.03 |
| Celgard K 381 | >1000 | 1.0 | 0.09 |
| Celgard K 359 | >1000 | 1.0 | 0.08 |
| Nuclepore polycarbonate (0.015$\mu$ pore size) | >1000 | 1.0 | 0.15 |
| Nuclepore polycarbonate | >1000 | 1.0 | 0.1 |

TABLE II-continued

| Membrane | $J_p$ µg/hr-cm² | $J_T/J_p$ | Voltage Drop volts |
|---|---|---|---|
| (0.05µ pore size) | | | |
| Nuclepore polycarbonate (0.1µ pore size) | >1000 | 1.0 | 0.14 |
| Nuclepore polycarbonate (0.4µ pore size) | >1000 | 1.0 | 0.065 |
| Nuclepore polycarbonate (1.0µ pore size) | >1000 | 1.0 | 0.18 |
| Nuclepore polyester (0.1µ pore size) | >1000 | 1.0 | 0.07 |
| Nuclepore polyester (0.4µ pore size) | >1000 | 1.0 | 0.05 |
| Nuclepore polyester (1.0µ pore size) | >1000 | 1.0 | 0.07 |
| Cellulose Acetate (20 wt % triacetin) | 1 | 1.0 | >30 |
| Cellulose Acetate (30 wt % triacetin) | 8 | 1.0 | >30 |
| Cellulose Acetate (40 wt % triacetin) | 1.5 | 1.0 | 1.3 |
| Vycor (35 mil thickness) | 300 | 2.0 | 1.5 |
| Vycor (62 mil thickness) | 75 | 1.0 | 0.3 |

*The $J_p$ and $J_T/J_p$ were not measured for the Celgard 2400 and 2500 membranes due to the high measured voltage drop.

None of the commercially available microporous membranes evaluated provided satisfactory results in all three properties of $J_p$, $J_T/J_p$ and voltage drop across the membrane. Either the voltage drop across the membrane was too high, as for some of the Celgard ® and cellulose acetate membranes, or the passive transport ($J_p$) of MCP greatly outweighed the electrokinetic transport $J_{EK}$) (i.e., the membranes had a $J_T/J_p$ ratio of about 1), thereby making the measured flux with and without applied current indistinguishable.

Likewise, none of the porous cellulose acetate membranes exhibited a $J_T/J_p$ ratio greater than 1.0. It is believed that the reason for the poor performance of these membranes in controlling the delivery of metaclopramide is because the molecular weight of the water soluble leachable triacetin (=218) was less than the molecular weight of the drug metaclopramide (=353).

COMPARATIVE EXAMPLE B

Commercial ion exchange membranes, of the type disclosed in Parsi U.S. Pat. No. 4,731,049 and Sanderson U.S. Pat. No. 4,722,726, were tested to determine their suitability for use as a control membrane in an iontophoretic drug delivery device. The membranes tested included both anion and cation exchange membranes. The anion exchange membranes tested were manufactured by RAI Research Corp. of Hauppauge, N.Y. and sold under the tradenames Raipore 1030, Raipore 4030 and Raipore 5030. The cation exchange membranes tested were Nafion ® manufactured by E.I. DuPont de Nemours & Co. of Wilmington, Del.; and Raipore 1010, Raipore 4010 and Raipore 5010 manufactured by RAI Research Corp..

The membranes were cut to size and then soaked in a saturated sodium chloride solution. This pretreatment ensured that the co-ion of the membranes fixed charge would be either sodium or chloride. The transport properties of these materials were measured as in Example I and are presented in Table III.

TABLE III

| Membrane | $J_p$ µg/hr-cm² | $J_T/J_p$ | Voltage Drop volts |
|---|---|---|---|
| Raipore 1030 | 400 | 1.0 | 0.25 |
| Raipore 4030 | 100 | 1.3 | 0.84 |
| Raipore 5030 | 140 | 1.1 | 0.15 |
| Nafion | 2.5 | 1.0 | >30 |
| Raipore 1010 | 1500 | 1.0 | 0.15 |
| Raipore 4010 | 180 | 2.7 | 0.4 |
| Raipore 5010 | 2.5 | 1.9 | 2 |

The anion exchange membranes all showed no appreciable difference in MCP flux for either passive or electrically-assisted transport (i.e., the membranes exhibited a $J_T/J_p$ ratio of about 1.0). The Nafion ® and Raipore 5010 membranes exhibited very small steady state MCP fluxes. The flux of MCP through Raipore 1010 indicated that the passive component exceeded the electrokinetic component to a large degree (i.e., the membrane exhibited a $J_T/J_p$ ratio of about 1) and therefore, both electrically-assisted and passive fluxes were comparable.

EXAMPLE II

The relationship between steady state total flux ($J_T$) during electrically assisted transport, the $J_T/J_p$ ratio and the voltage drop across the membrane was evaluated for a composite membrane comprised of 18 vol % Chelex ®100 (particle size smaller than 400 mesh) and 82 vol % EVA 40. Table IV shows the range for measured voltage drop across the membrane and of the average measured $J_T$ values for MCP.

TABLE IV

| Current Density µA/cm² | Voltage Drop volts | $J_T$ µg/cm²-hr. |
|---|---|---|
| 50 | 0.14 | 73 |
| 100 | 0.29 | 142 |
| 200 | 0.36 | 276 |
| 300 | 2.90 | 441 |
| 417 | 0.24 | 644 |
| 625 | 1.06 | 948 |

The magnitude of the passive flux was dependent on the volume fraction of resin within the membrane. However, the electrically-assisted flux was independent of this quantity. Therefore, the $J_T/J_p$ ratio can be predicted from the volume fraction of resin and other measurable quantities. This is illustrated in the following example.

EXAMPLE III

Twenty composite control membranes were studied. Each of the membranes was composed of a mixture of hydrophobic EVA 40 matrix and one of the following hydrophilic resins: Chelex ®100 (particle size smaller than 400 mesh), Chelex ®100 (particle size of 100–200 mesh), Bio-Rex ®70 and PVP. Each of the composite membranes is represented by a data point in FIG. 6. The composition for each of the twenty membranes may be determined by measuring the abscissa of each data point, calculating the volume fraction of hydrophilic resin, and then subtracting the volume fraction of hydrophilic resin from 1 to determine the volume fraction of the EVA-40 matrix. The total flux ($J_T$) and the flux due to passive diffusion ($J_p$) were measured and the $J_T/J_p$ ratio for each membrane was calculated and plotted against the reciprocal of the volume fraction of hydrophilic resin. The results are presented in FIG. 6.

Figure 6:
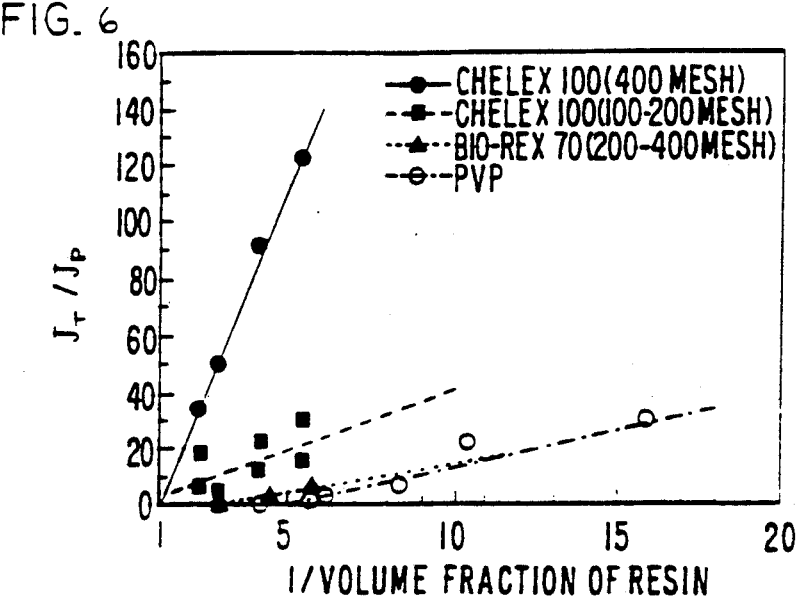
FIG. 6 is a graph illustrating the effect of hydrophilic resin loading on the ratio of electrically-assisted flux-to-passive flux for the drug metoclopramide through various membranes of the present invention.

The slopes of the curves presented in FIG. 6 were calculated using a linear regression best fit analysis and are presented in Table V. It is possible to compare the slopes directly because all experimental parameters (temperature, donor concentration, current density, membrane thickness) were identical in determining the $J_T/J_p$ ratios plotted in FIG. 6. Thus, Chelex ®100 having a particle size smaller than 400 mesh was the most effective for controlling the passive diffusion of MCP.

TABLE V

| Resin | Slope |
| --- | --- |
| Chelex ®100 (smaller than 400 mesh) | 28.5 |
| Chelex ®100 (100-200 mesh) | 4.03 |
| Bio-Rex ®70 | 1.96 |
| PVP | 2.87 |

EXAMPLE IV

A control membrane in accordance with the present invention was formed by dissolving 20.0 g of cellulose acetate 398-10 (sold by Eastman Kodak, Co. of Rochester, N.Y.) and 3.53 g polyethylene glycol having a molecular weight of 8000 in 150 ml of a solvent composed of 93% methylene chloride and 7% methanol. The mixture was pored onto a glass plate and spread with a Gardner knife to a thickness of about 70 mils. The membrane was allowed to air dry at room temperature overnight. The formed membrane had a thickness of about 7 mils. The membrane was then soaked overnight in water until substantially all of the polyethylene glycol had leached out. The leaching left a cellulose acetate membrane having a pore volume of slightly less than 15%.

The membrane properties $J_p$, $J_T$ and voltage drop across the membrane were measured in accordance with the procedures used in Example I. The membrane was found to have the following properties:

$J_p = 0.95$ μg/hr-cm$^2$;

$J_T/J_p = 14.2$; and

Voltage drop across the membrane = 0.5±0.2 volts.

Having thus generally described our invention and described in detail certain preferred embodiments thereof, it will be readily apparent that various modifications to the invention may be made by those skilled in the art without departing from the scope of this invention and which is limited only by the following claims.

What is claimed is:

1. An iontophoretic agent delivery electrode for placement on a body surface and for delivering an agent through the body surface, comprising:
   a reservoir containing the agent to be delivered;
   conductive means for electrically connecting the reservoir to a source of electrical power;
   a means for maintaining the reservoir in agent transmitting relationship to said body surface; and
   a membrane interposed between the agent reservoir and the body surface, the membrane permitting electrically-assisted flux ($J_{EK}$) of the agent therethrough and substantially preventing passive flux ($J_p$) of the agent therethrough, the membrane exhibiting a ($J_{EK}+J_p$)/$J_p$ ratio of at least about 4, a voltage drop across the membrane of less than about 1 volt, and a $J_p$ of less than about 100 μg/hr-cm$^2$.

2. The electrode of claim 1, wherein the body surface is selected from the group consisting of skin and mucosal membranes.

3. The electrode of claim 1, wherein the agent comprises a drug.

4. The electrode of claim 1, wherein the agent is selected from the group consisting of peptides, polypeptides and proteins.

5. The electrode of claim 1, wherein the membranes 11/33 to 12/12 is comprised of a material selected from the group consisting of polycarbonates, polyesters, polyamides, styrene-acrylic acid copolymers, polyurethanes, cellulose ester and polyalkylenes.

6. The electrode of claim 1, wherein the membrane comprises a mixture of a hydrophilic resin and a hydrophobic polymer.

7. The electrode of claim 6, wherein the mixture comprises about 10 to 30 vol % hydrophilic resin.

8. The electrode of claim 6, wherein said hydrophilic resin comprises polyvinylpyrrolidone.

9. The electrode of claim 6, wherein said hydrophilic resin comprises an ion exchange resin.

10. The electrode of claim 6, wherein said hydrophobic polymer comprises an ethylene vinyl acetate copolymer having a vinyl acetate content in the range of about 1 to 40 weight percent.

11. An iontophoretic agent delivery device for placement on a body surface comprising:
    a donor electrode including a reservoir containing the agent to be delivered, a counter electrode and a source of electrical power electrically connected to the donor and counter electrodes, the donor and counter electrodes adapted to be placed in spaced apart relationship on the body surface;
    means for maintaining the agent reservoir in agent transmitting relation with the body surface and for maintaining the counter electrode in electrolyte transmitting relation with the body surface; and
    a membrane interposed between the agent reservoir and the body surface, the membrane permitting electrically-assisted flux ($J_{EK}$) of the agent therethrough and substantially preventing passive flux ($J_p$) of the agent therethrough, the membrane exhibiting a ($J_{EK}+J_p$)/$J_p$ ratio of at least about 4, a voltage drop across the membrane of less than about 1 volt, and a $J_p$ of less than about 100 μg/hr-cm$^2$.

12. The device of claim 11, wherein the body surface is selected from the group consisting of skin and mucosal membranes.

13. The device of claim 11, wherein the agent comprises a drug.

14. The device of claim 11, wherein the agent is selected from the group consisting of peptides, polypeptides and proteins.

15. The device of claim 11, wherein the membrane is comprised of a material selected from the group consisting of polycarbonates, polyesters, polyamides, styrene-acrylic acid copolymers, polyurethanes, cellulose esters and polyalkylenes.

16. The device of claim 11, wherein the membrane comprises a mixture of a hydrophilic resin and a hydrophobic polymer.

17. The device of claim 16, wherein the mixture comprises about 10 to 30 vol % hydrophilic resin.

18. The device of claim 16, wherein the hydrophilic resin comprises polyvinylpyrrolidone.

19. The device of claim 16, wherein the hydrophilic resin comprises an ion exchange resin.

20. The device of claim 16, wherein said hydrophobic polymer comprises a ethylene vinyl acetate copolymer having a vinyl acetate content in the range of about 1 to 40 weight percent.

21. A membrane for controlling agent delivery rom an iontophoretic agent delivery device adapted to deliver the agent through an intact body surface, the device having a reservoir containing the agent to be delivered and being connectable to a source of electrical power for driving the agent from the reservoir and through the body surface, wherein the membrane is interposed between the agent reservoir and the body surface, the membrane permitting electrically-assisted flux ($J_{EK}$) of the agent therethrough and substantially preventing passive flux ($J_p$) of the agent therethrough, the membrane exhibiting a ($J_{EK}+J_p$)/$J_p$ ratio of at least about 4, a voltage drop across the membrane of less than about 1 volt, and a $J_p$ of less than about 100 µg/hr-cm².

22. The membrane for claim 21, wherein the agent comprises a drug.

23. The membrane of claim 1, wherein the membrane is comprised of a material selected from the group consisting of polycarbonates, polyesters, polyamides, styrene-acrylic acid copolymers, polyurethanes, cellulose esters and polyalkylenes.

24. The membrane of claim 21, comprising a mixture of a hydrophilic resin and a hydrophobic polymer.

25. The membrane of claim 24, wherein the mixture comprises about 10 to 30 vol % hydrophilic resin.

26. The membrane of claim 24, wherein the hydrophilic resin is selected from the group consisting of hydrophilic polymers having an equilibrium water content of at least about 10%.

27. The membrane of claim 26, wherein said hydrophilic resin comprises polyvinylpyrrolidone.

28. The membrane of claim 24, wherein said hydrophilic resin comprises an ion exchange resin.

29. The membrane of claim 28, wherein said ion exchange resin has a functional group selected from the group consisting of sulfonic acid, carboxylic acid, imidodiacetic acid and quaternary amines.

30. The membrane of claim 24, wherein the hydrophobic polymer is selected from the group consisting of polymers having an equilibrium water content of less than about 10%.

31. The membrane of claim 24, wherein said hydrophobic polymer comprises an ethylene vinyl acetate copolymer having a vinyl acetate content in the range of about 1 to 40 weight percent.

32. A membrane for testing performance characteristics of an iontophoretic agent delivery device adapted for delivering an agent through an intact body surface, the device having a reservoir containing the agent to be delivered and being connectable to a source of electrical power for driving the agent from the reservoir and through the body surface, the membrane permitting electrically-assisted flux ($J_{EK}$) of the agent therethrough and substantially preventing passive flux ($J_p$) of the agent therethrough, the membrane exhibiting a ($J_{EK}+J_p$)/$J_p$ ratio of at least about 4, a voltage drop across the membrane of less than about 10 volts and a $J_p$ of less than about 100 µg/hr-cm².

33. The membrane of claim 32, wherein the agent comprises a drug.

34. The membrane of claim 32, wherein the membrane 11/33 to 12/12 is comprised of a material selected from the group consisting of polycarbonates, polyesters, polyamides, styrene-acrylic acid copolymers, polyurethanes, cellulose esters and polyalkylenes.

35. The membrane of claim 32, comprising a mixture of a hydrophilic resin and a hydrophobic polymer.

36. The membrane of claim 35, wherein the mixture comprises about 10 to 30 vol % hydrophilic resin.

37. The membrane of claim 35, wherein the hydrophilic resin is selected from the group consisting of hydrophilic polymers having an equilibrium water content of at least about 10%.

38. The membrane of claim 37, wherein said hydrophilic resin comprises polyvinylpyrrolidone.

39. The membrane of claim 35, wherein said hydrophilic resin comprises an ion exchange resin.

40. The membrane of claim 38, wherein said ion exchange resin has a functional group selected from the group consisting of sulfonic acid, carboxylic acid, imidodiacetic acid and quaternary amines.

41. The membrane of claim 35, wherein the hydrophobic polymer is selected from the group consisting of polymers having an equilibrium water content of less than about 10%.

42. The membrane of claim 35, wherein the hydrophobic polymer comprises an ethylene vinyl acetate copolymer having a vinyl acetate content in the range of about 1 to 40 weight percent.

43. A method for testing performance characteristics of an iontophoretic agent delivery device adapted for delivering an agent through an intact body surface, the device having a reservoir containing the agent to be delivered and being connectable to a source of electrical power for driving the agent from the reservoir, comprising:

placing the reservoir in agent transmitting relation with one surface of a membrane, the membrane having a second surface opposite the surface which is in agent transmitting relation with the reservoir, which second surface is in contact with an agent collecting medium, the membrane permitting electrically-assisted flux ($J_{EK}$) of the agent therethrough and substantially preventing passive flux ($J_p$) of the agent therethrough, the membrane exhibiting a ($J_{EK}+J_p$)/$J_p$ ratio of at least about 4, a voltage drop across the membrane of less than about 10 volts, and a $J_p$ of less than about 100 µg/hr-cm²; and connecting the source of electrical power to the device and driving the agent through the membrane.

44. The method of claim 43, wherein the agent comprises a drug.

45. The method of claim 43, wherein the membrane 11/33 to 12/12 is comprised of a material selected from the group consisting of polycarbonates, polyesters, polyamides, styrene-acrylic acid copolymers, polyurethanes, cellulose esters and polyalkylenes.

46. The method of claim 43, wherein the membrane comprises a mixture of a hydrophilic resin and a hydrophobic polymer.

47. The method of claim 46, wherein the mixture comprises about 10 to 30 vol % hydrophilic resin.

48. The method of claim 46, wherein the hydrophilic resin is selected from the group consisting of hydrophilic polymers having an equilibrium water content greater than about 10%.

49. The method of claim 46, wherein said hydrophilic resin is polyvinylpyrrolidone.

50. The method of claim 46, wherein said hydrophilic resin is an ion exchange resin.

51. The method of claim 50, wherein said ion exchange resin has a functional group selected from the group consisting of sulfonic acid, carboxylic acid, imidodiacetic acid and quaternary amines.

52. The method of claim 46, wherein the hydrophobic polymer is selected from the group consisting of polymers having an equilibrium water content of less than about 10%.

53. The method of claim 46, wherein the hydrophobic polymer comprises an ethylene vinyl acetate copolymer having a vinyl acetate content in the range of about 1 to 40 weight percent.

* * * * *